US008077872B2

(12) United States Patent
Dyer et al.

(10) Patent No.: US 8,077,872 B2
(45) Date of Patent: Dec. 13, 2011

(54) HEADSET VISUAL FEEDBACK SYSTEM

(75) Inventors: Medford Alan Dyer, San Diego, CA (US); Jerry J. Harvey, Newport Beach, CA (US); Robert G. Allison, San Juan Capistrano, CA (US)

(73) Assignee: Logitech International, S.A. (CH)

( * ) Notice: Subject to any disclaimer, the term of this patent is extended or adjusted under 35 U.S.C. 154(b) by 1299 days.

(21) Appl. No.: 11/353,813

(22) Filed: Feb. 13, 2006

(65) Prior Publication Data

US 2006/0222185 A1 Oct. 5, 2006

Related U.S. Application Data

(60) Provisional application No. 60/668,289, filed on Apr. 5, 2005.

(51) Int. Cl.

| | |
|---|---|
| ***H04R 29/00*** | (2006.01) |
| ***H04R 1/10*** | (2006.01) |
| ***H03G 11/00*** | (2006.01) |
| ***A61F 11/06*** | (2006.01) |

(52) U.S. Cl. ................. 381/56; 381/55; 381/72; 381/74

(58) Field of Classification Search .................... 381/55, 381/56, 72, 74

See application file for complete search history.

(56) References Cited

U.S. PATENT DOCUMENTS

| | | | | |
|---|---|---|---|---|
| 3,549,808 | A * | 12/1970 | Smith | 381/55 |
| 4,143,245 | A * | 3/1979 | Scholz | 381/109 |
| 5,134,659 | A * | 7/1992 | Moseley | 381/72 |
| 5,727,070 | A * | 3/1998 | Coninx | 381/321 |
| 2003/0002688 | A1* | 1/2003 | Kanevsky et al. | 381/74 |
| 2004/0190729 | A1* | 9/2004 | Yonovitz et al. | 381/72 |

* cited by examiner

*Primary Examiner* — Vivian Chin

*Assistant Examiner* — Douglas Suthers

(74) *Attorney, Agent, or Firm* — Patent Law Office of David G. Beck

(57) ABSTRACT

A visual feedback system that activates a visual display when the sound pressure level from a headset attached to the system exceeds a preset level is provided, along with a method of using the same. The visual feedback system is interposed between the audio source and the headset and is either integral to a specific headset or coupleable to any of a variety of headsets. If a non-integral headset is used with the visual feedback system, the system is matched to the characteristics of the selected headset, for example using a selector switch or via a calibration process. During operation, the visual feedback system illuminates a display (e.g., an LED) whenever the sound pressure level from the attached headset exceeds the preset level. The visual feedback system can be implemented using analog or digital circuitry.

17 Claims, 9 Drawing Sheets

HEADSET VISUAL FEEDBACK SYSTEM

CROSS-REFERENCES TO RELATED APPLICATIONS

This application claims the benefit of U.S. Provisional Patent Application Ser. No. 60/668,289, filed Apr. 5, 2005, the disclosure of which is incorporated herein by reference for any and all purposes.

FIELD OF THE INVENTION

The present invention relates generally to audio headsets.

BACKGROUND OF THE INVENTION

Hearing loss is currently the third most prevalent chronic condition in the elderly with an estimated 25 to 40 percent of the people in this country over the age of 60 suffering from a hearing impairment. In total, approximately 28 million Americans have a hearing impairment. Arguably of greater concern is the fact that hearing loss is on the rise among people of all ages. For example, one National Health survey found that from 1971 to 1990, hearing problems for people between the ages of 45 and 64 have increased by 26 percent while people between the ages of 18 and 44 experienced a 17 percent increase during the same time. In a survey of people in their 50's living in California, researchers found that the rate of impairment jumped 150 percent between 1965 and 1994. A study by the American Medical Association reported that approximately 15 percent of school-aged children have a hearing loss.

Sensorineural hearing loss, which accounts for approximately 90 percent of all hearing loss, can be caused by old age, Menieres disease, ototoxic medications and noise exposure. It is this last cause, noise exposure, which is the likely cause of the current trend of increasing hearing loss. In general, the environment today is much noisier than in the past, the increase due to a variety of sources ranging from machinery (e.g., cars, power tools, lawn mowers, leaf blowers, vacuum cleaners, etc.) to personal entertainment systems (Walkmans, iPods, MP3 players, etc.). Furthermore, these sources of noise are very pervasive, exposing people to high noise levels in the workplace, in recreational settings and at home, providing people with little time to rest their ears.

Noise induced hearing loss (NIHL) is the result of both the sound pressure level (SPL), measured in decibels (dB), and the length of exposure. Accordingly, a person can tolerate a much longer exposure to a lower sound level than to a higher sound level. For example, OSHA (Occupational Safety and Health Administration) estimates that a person can tolerate up to 8 hours per day of a 90 dB sound (e.g., subway train, hair dryer, lawn mower), 2 hours per day of a 100 dB sound source (e.g., chain saw, pneumatic drill), and only a half an hour of a 110 dB sound (e.g., dance club), before experiencing some degree of permanent hearing loss. To make matters worse, except in those cases where a person is exposed to an extremely loud sound such as a gunshot at approximately 165 dB or a firecracker at approximately 180 dB, hearing loss is a very gradual phenomenon in which the effects are cumulative and relatively symptom-less. Accordingly, most people are unaware that they are exposing themselves to ear-damaging sound levels.

It is generally believed that the use of headphones and earbuds has contributed to the rise in hearing loss, especially in younger people. Although in part this may be due to the close proximity of the transducers to the ears, the primary reason appears to be that most users typically listen at very high volume levels. For example, a survey by Australia's National Acoustic Laboratories found that approximately 25 percent of the people that use a portable stereo on a daily basis listen at volume levels high enough to cause hearing loss. Users of headphones and earbuds also appear to be more susceptible to threshold shifting wherein the user adapts to the current volume level and thus increases the volume level to reach the same perceived level, thereby increasing the risk of hearing damage.

Another aspect of typical headphone and earbud use that heightens the risk of hearing loss is that most users turn up the volume in an attempt to drown out background sounds. For example, a recent study found that in a quiet laboratory setting users set their volume level to an average volume of 69 dB, a very safe level. However when the background level was increased to 65 dB, the average volume went up to 82 dB, with some users increasing the volume level to as high as 95 dB. Considering that the noise level generated by city traffic is approximately 80 dB, one may assume that users would turn up the volume on their headsets to an even higher, and more dangerous, level under normal background conditions.

To date, there have been a couple of different approaches taken to lowering the risks of hearing loss when using headphones and earbuds. The first approach is one of public education, both in terms of the risks associated with exposure to loud noises and possible ways of minimizing these risks. The second approach is the use of high quality, in-ear monitors that provide vastly improved ambient noise attenuation, thus allowing the user to listen to their stereo at a safe volume level. Although both approaches are viable, they still require the user to recognize when they are exposing themselves to potentially damaging sound levels. Accordingly, what is needed in the art is an apparatus that visually indicates when the sound level is at a dangerous level. The present invention provides such an apparatus.

SUMMARY OF THE INVENTION

The present invention provides a visual feedback system, and method of using same, which provides a visual indicator when the sound pressure level from a headset attached to the system exceeds a preset level. The visual feedback system of the invention is interposed between the audio source and the headset and is either integral (i.e., hard-wired) to a specific headset, or coupleable to any of a variety of headsets, for example using a common plug and jack arrangement. If a non-integral headset is used with the visual feedback system, the system is matched to the characteristics of the selected headset, for example using a selector switch or via a calibration process.

During operation, the visual feedback system illuminates a display (e.g., an LED) whenever the sound pressure level from the attached headset exceeds the preset level. As such, preferably the display of the system is located in an easily observed location, for example at the union of the left and right audio channel cables. In at least one embodiment, the display, and preferably the entire visual feedback system, is contained within the same enclosure as that used to house a volume controller, thus allowing the user to monitor whether or not the preset level has been exceeded while adjusting the headset volume.

In at least one embodiment, in addition to indicating via the display that the preset sound level has been exceeded, the system attenuates the output SPL.

In at least one embodiment, the display coupled to the visual feedback system includes multiple display indicators (e.g., LEDs). Preferably each display indicator corresponds to a different preset sound pressure level, thus providing the user with additional information regarding the sound pressure level output by the headset.

In at least one embodiment, the visual feedback system includes sufficient memory to maintain a history of each time the sound pressure level exceeds the preset level or levels. Preferably the extent by which the preset level is exceeded and/or the duration of SPL excursion are recorded.

In at least one embodiment, the visual feedback system is implemented using analog circuitry, for example utilizing a pair of LEDs between the signal line for each audio channel and the common line. In at least one other embodiment, the visual feedback system is implemented using digital circuitry, for example a digital signal processor.

A further understanding of the nature and advantages of the present invention may be realized by reference to the remaining portions of the specification and the drawings.

DESCRIPTION OF THE SPECIFIC EMBODIMENTS

A number of governmental agencies such as the FDA (Food and Drug Administration), OSHA (Occupational Safety and Health Administration), EPA (Environmental Protection Agency), NIOSH (National Institute for Occupational Safety and Health), and the NIDCD (National Institute on Deafness and Other Communication Disorders) as well as a number of private, non-profit organizations such as ASHA (American Speech-Language-Hearing Association), NHCA (National Hearing Conservation Association), ATA (American Tinnitus Association), and HEAR (Hearing Education and Awareness for Rockers) attempt to combat noise induced hearing loss (NIHL) through educational programs. Such programs describe the sources of noise, both intentional (e.g., portable stereo, etc.) and unintentional (e.g., traffic, power tools, etc.), that can lead to hearing loss as well as methods of minimizing these risks. Typically these programs also set NIHL thresholds that are based both on sound pressure level (SPL) and exposure time. Unfortunately, without the aid of a sound meter it is difficult to determine the SPL, or volume, of a personal stereo (e.g., iPod, Walkmans, MP3 player, etc.). Thus even the best-intentioned user may still subject themselves to potentially damaging sound levels.

Figure 1:
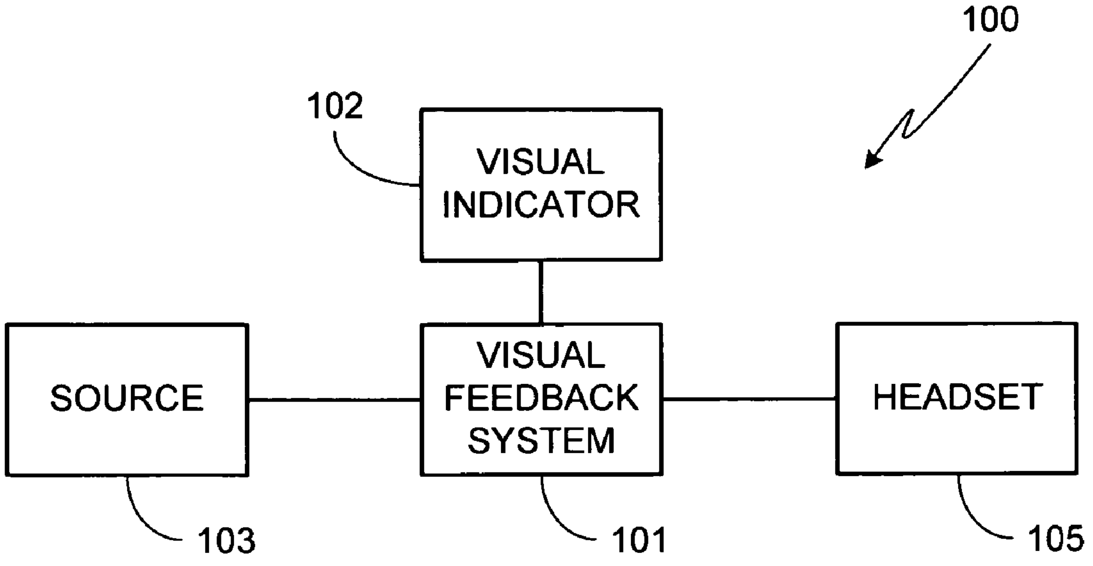
FIG. 1 is a conceptual illustration of the invention.

FIG. 1 conceptually illustrates the invention, an apparatus that overcomes the afore-described problem. As shown, system 100 includes a visual feedback system 101 that is interposed between the source 103 and the user's headset 105. Source 103 can be any audio source, such as a Walkman, iPod, MP3 player or other personal, portable device. It should be appreciated, however, that the inventors envision the use of the present invention with other audio sources that may not be portable. For example, visual feedback system 101 can be used with an audio mixing board, thus allowing audio engineers to monitor their own SPL levels. It should also be appreciated that the invention is not limited to a specific style of headset and as such, headset 105 refer to in-ear monitors, earpieces, canal phones and headphones. Furthermore although typically a headset includes a pair of monitors (i.e., left ear/right ear), the invention can also be used with a single earpiece/headphone.

Visual feedback system 101 includes a visual display 102 that provides the user with a visual indication when the SPL, i.e., volume level, is above a preset level. Visual display 102 is preferably a simple lighting arrangement (e.g., an LED, miniature incandescent light, etc.), thus insuring that the user can quickly determine whether or not the current volume level is above the preset level. The preset level used in the invention is tied to a specific, potentially damaging sound level (e.g., 100 dB). As feedback system 101 does not indicate by how much the volume exceeds the preset level, it will be appreciated that if the preset level is set at 100 dB, the visual indicator will be activated whether the volume level is 100 dB or 120 dB. Accordingly, the purpose of visual feedback system 101 is to warn the user to reduce the volume level to minimize the risk of hearing loss. This is in stark contrast to audio equipment that use a series of LEDs to simply indicate the relative volume level, either to achieve the desired sound mix (e.g., recording decks, mixing boards) or for decorative purposes (e.g., the light display on some portable receivers/decks).

Figure 4:
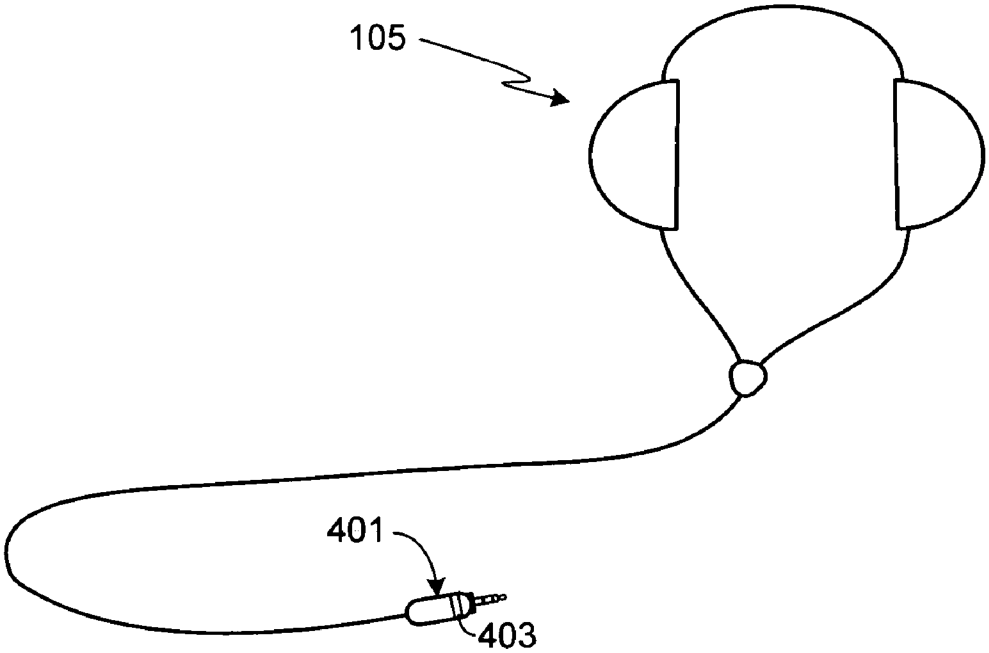
FIG. 4 is an illustration of an embodiment in which the visual feedback system is contained within the headphone plug assembly.
Figure 5:
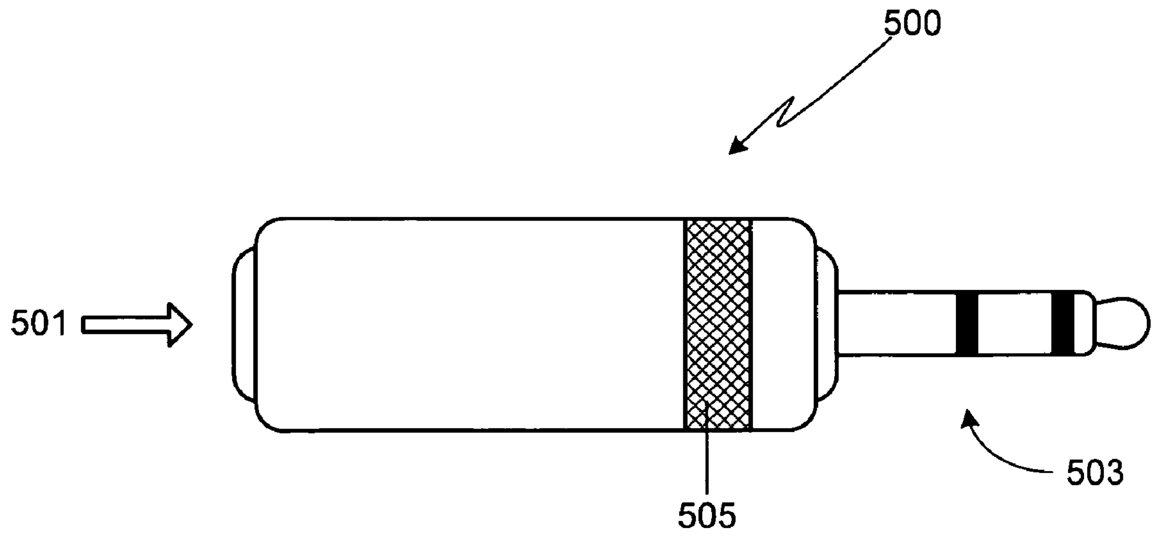
FIG. 5 is an illustration of an embodiment in which the visual feedback system is contained within a headphone plug assembly that is separate from the headset.
Figure 6:
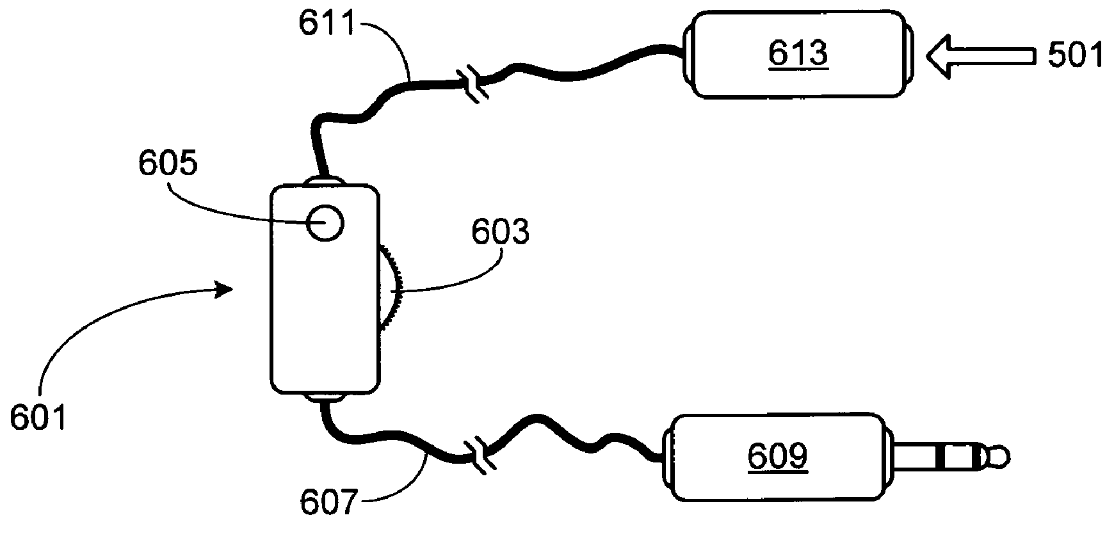
FIG. 6 is an illustration of an embodiment in which the visual feedback system is contained within a housing that is separate from the headset, the housing also including a volume control.

The present invention can be implemented in a variety of ways ranging from systems that are integral to a headset (e.g., FIGS. 2-4) to those that are intended to be added to an existing headset (e.g., FIGS. 5 and 6). In the exemplary embodiment shown in FIG. 2, visual feedback system 201 is integrated within the audio cable 203 that couples the input device (not shown) to headset 105. Preferably, feedback system 201 is located within audio cable 203 at an easily observed location. For example in the illustrated embodiment, feedback system 201 is located at the union of left channel cable 205 and right channel cable 206. In this embodiment, the visual display is a single LED 207 that is used by feedback system 201 to indicate when the volume exceeds the preset level (i.e., when the volume is set to an excessive, potentially damaging, level).

Figure 3:
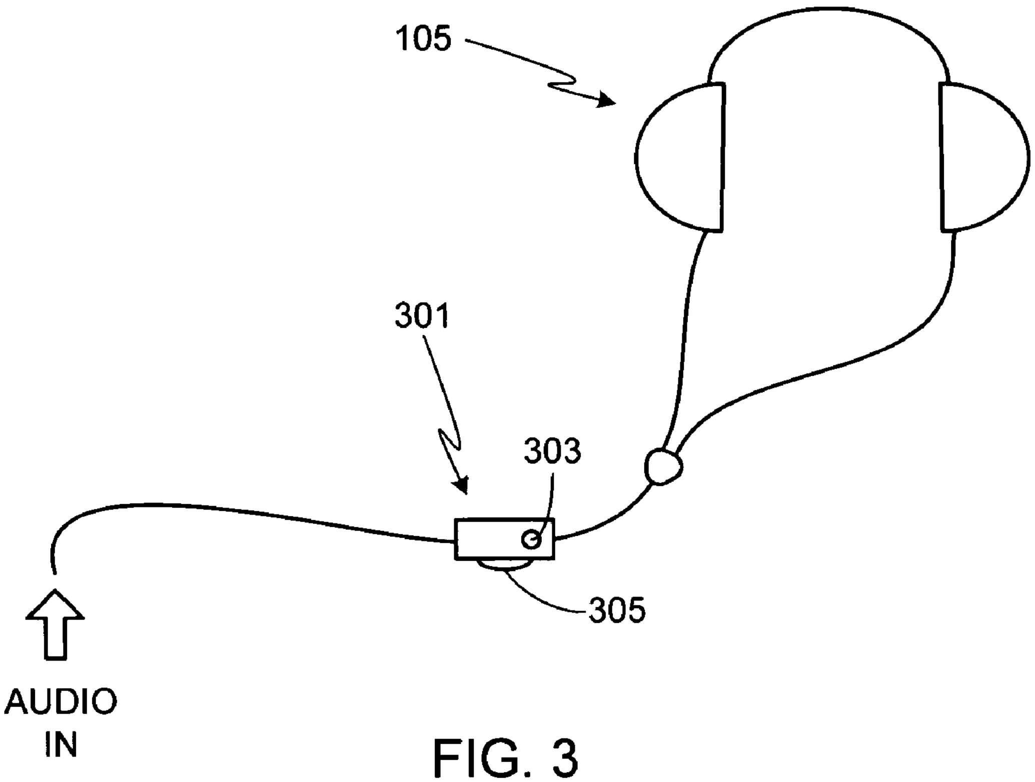
FIG. 3 is an illustration of an embodiment in which the visual feedback system is combined within the same housing as an in-line volume controller.

In an alternate exemplary embodiment shown in FIG. 3, the visual feedback system is contained within the same housing 301 as an in-line volume controller. In addition to providing a compact design, this configuration gives the user an immediate indication via visual feedback display 303 (e.g., an LED) if the in-line volume switch 305 is turned to a potentially hearing damaging level (i.e., one that exceeds the preset level).

In an alternate exemplary embodiment shown in FIG. 4, the visual feedback system is combined within the headphone plug assembly 401. Although the visual feedback system can utilize any of a variety of visual display configurations, in a preferred embodiment the visual display is a semi-transparent ring 403 around the perimeter of assembly 401. One or more LEDs contained within assembly 401 illuminate ring 403 when the feedback system determines that the SPL exceeds the preset level.

Figure 2:
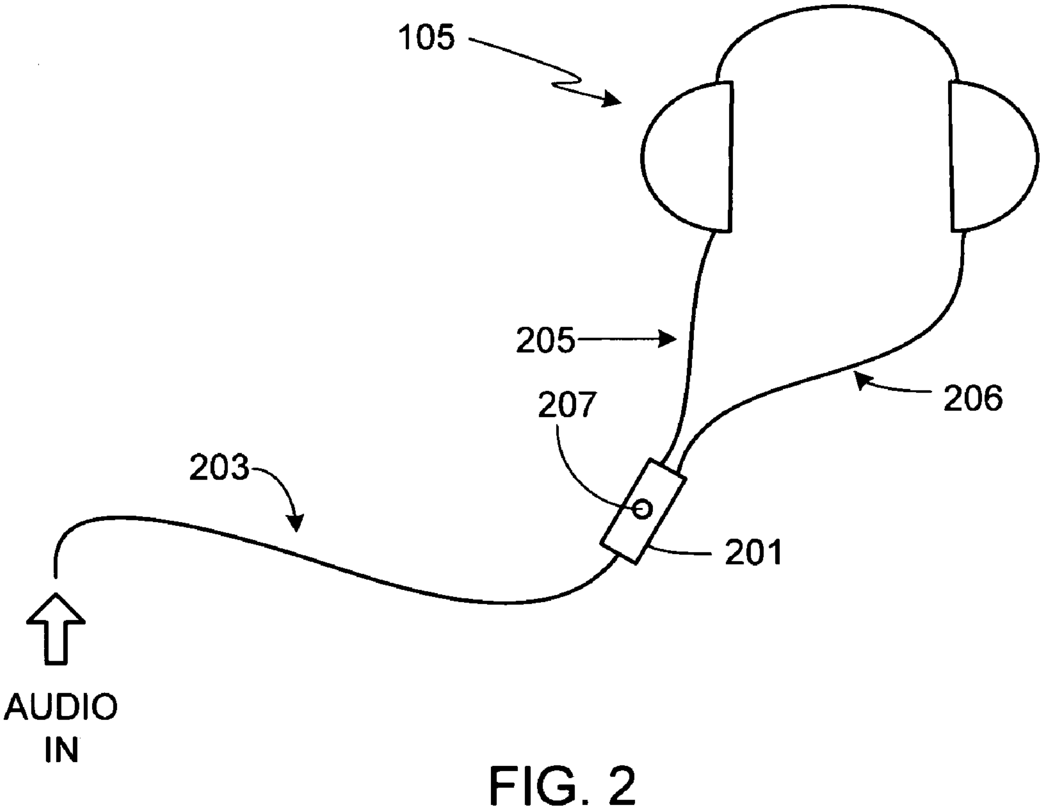
FIG. 2 is an illustration of an embodiment in which the visual feedback system is located at the intersection of the left and right headset channel cables.

FIGS. 5 and 6 illustrate exemplary embodiments of visual feedback systems in accordance with the invention that are designed to be used with a pre-existing headset, i.e., the visual feedback system is not integrated into the headset system as illustrated in FIGS. 2-4. For example, in the embodiment illustrated in FIG. 5 a headphone plug assembly 500 is shown. The cable plug from the headset (not shown) plugs into a jack within the end of assembly 500 as shown by arrow 501 while assembly plug 503 plugs into the desired audio source (not shown). When the signal level passing through assembly 500 from the audio source to the headset exceeds the preset level, a visual display 505 is illuminated, thus warning the user that the sound level has exceeded the preset level. As illustrated, visual display 505 is a semi-transparent ring that is illuminated by one or more LEDs within assembly 500 when triggered by the feedback system. Alternate embodiments can utilize one or more externally mounted LEDs or other light emitting devices. In the alternate embodiment shown in FIG. 6, the housing 601 containing the visual feedback system also contains a volume controller. Therefore as in the integrated embodiment shown in FIG. 3, when the user adjusts the volume, for example via a thumb wheel 603, they are given immediate feedback via the feedback system and visual display 605 whether or not the selected volume level causes the volume to exceed the preset level. Although both a headphone jack and plug can be included in housing 601 thus allowing the assembly to be used much as the embodiment shown in FIG. 5, preferably housing 601 is electrically coupled via audio cable 607 to a headphone plug 609, and electrically coupled via audio cable 611 to a headphone jack 613 as illustrated. A benefit of this configuration is that it allows the user easy access to the volume controller and helps to insure the visibility of indicator light 605.

As those of skill in the art will appreciate, setting the preset level to a specific SPL requires knowledge of the operating characteristics (e.g., impedance) of the headset for which the visual feedback system is to be used. This task is not difficult when the visual feedback system and the headset are combined into a single system such as those shown in FIGS. 2-4. However when the visual feedback system and the headset are separate, as in the embodiments shown in FIGS. 5 and 6, the task becomes more difficult.

Figure 7:
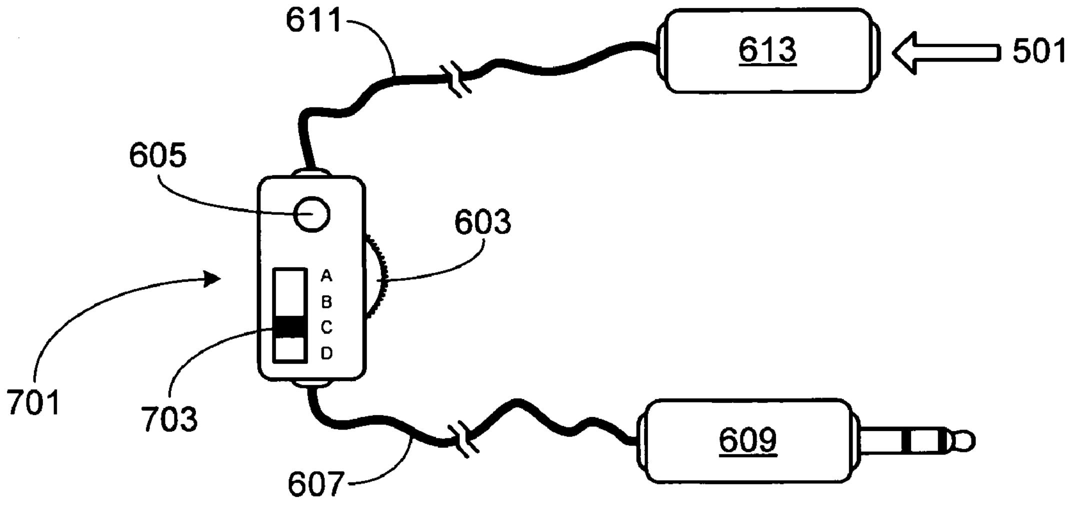
FIG. 7 is an illustration of an embodiment similar to that shown in FIG. 6, except for the inclusion of an impedance selector switch that allows the system to be used with a variety of headsets.

One approach to achieving accurate preset levels for a non-integrated visual feedback system is to manufacture multiple systems, each designed for use with a specific impedance headset. A simple cross-reference chart then allows the end user to determine the appropriate feedback system for their headset. In an alternate approach, a switch is integrated with the visual feedback system, allowing it to be matched to different impedance headsets. Such a system 701 is shown in FIG. 7, slide switch 703 providing the user with multiple impedance-matching settings from which to select. Embodiments of the visual feedback system that utilize an impedance selector switch do not have to include a volume controller as shown.

Although the visual feedback system of the invention can be used with non-integrated headsets by properly matching the feedback system to the headset as described above, in an alternate approach a calibration microphone (e.g., microphone 801 in FIGS. 8 and 9), preferably removable, is attached to the visual cavitation system and used to calibrate the system to the characteristics of the headset. In use, the user attaches their headset to the visual feedback system, properly positions the calibration microphone relative to the headset, plays an appropriate source, and then calibrates the feedback system. Feedback system calibration can be automatic, for example using a reset button (e.g., reset button 803 in the embodiment shown in FIG. 8), or manual (e.g., for example by rotating a miniature potentiometer 901 as shown in FIG. 9).

Figure 8:
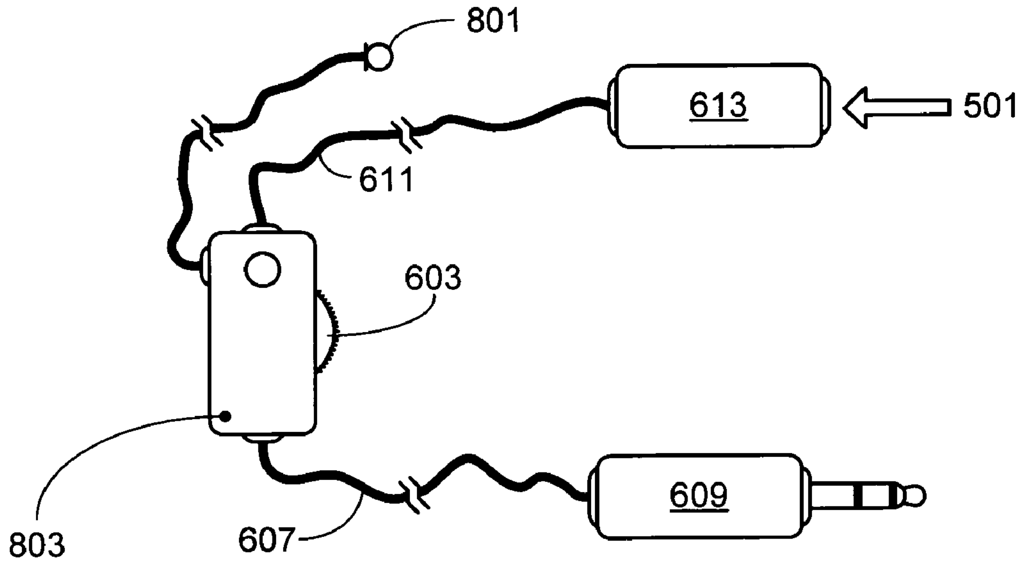
FIG. 8 is an illustration of an embodiment similar to that shown in FIG. 6, except for the inclusion of a calibration microphone and a reset switch.
Figure 9:
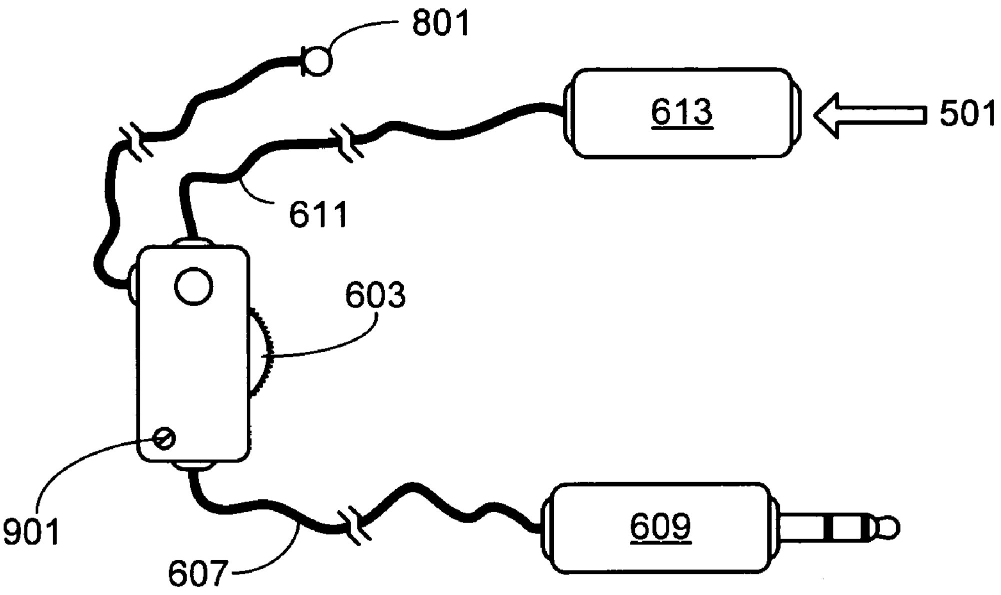
FIG. 9 is an illustration of an embodiment similar to that shown in FIG. 8, except for the inclusion of a manually settable calibration switch.
Figure 10:
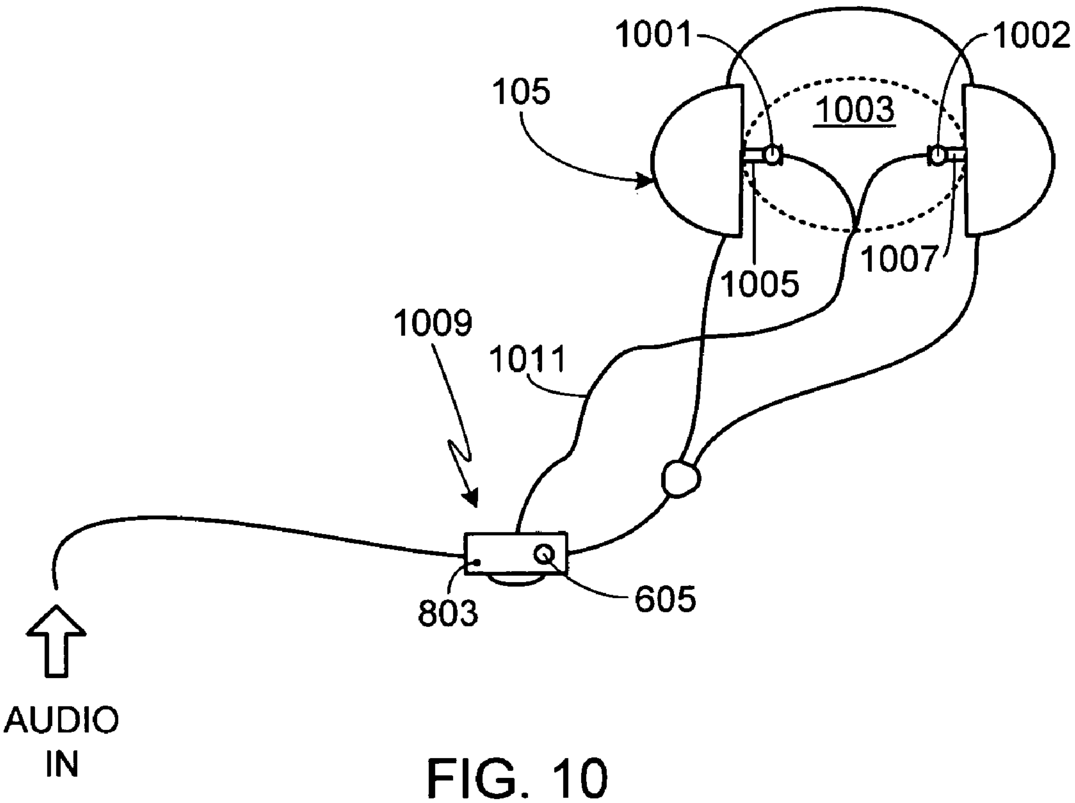
FIG. 10 is an illustration of an embodiment of the invention in which calibration microphones integrated into an ear simulator are used to calibrate the preset sound pressure levels of the visual feedback system for a non-integrated headset.

It will be appreciated by those of skill in the art that the accuracy of calibrating the visual feedback system using a calibration microphone as in the embodiments shown in FIGS. 8 and 9 is dependent, in part, on the ability of the calibration microphone to receive the same sound pressure level as a human ear. Accordingly, microphone placement is very important. In a preferred embodiment illustrated in FIG. 10, a pair of calibration microphones 1001/1002 is located within an ear simulator 1003 (note ear simulator 1003 is shown in phantom). Within ear simulator 1003 are two ear simulation tubes 1005/1007 which couple microphones 1001/1002, respectively, to openings in ear simulator 1003. Ear simulation tubes 1005/1007 properly position the calibration microphones relative to the headset speakers. If headset 105 is comprised of in-ear monitors, the in-ear monitors are positioned within ear simulation tubes 1005/1007 in the same manner as the user would normally position the in-ear monitors within their ear canals. Thus the sealed conditions, as well as the proximity of the headset drivers to the ear drums, can be simulated. If headset 105 is comprised of headphones, the headphone cans are positioned on the outside of simulator 1003, once again simulating the position of the headset relative to the ear drums of an actual user. Ear simulator 1003, with integral microphones 1001/1002, is temporarily connected to visual feedback system 1009 by cable 1011. Preferably calibration of visual feedback system 1009 is automatic, for example using a reset switch 803 as shown.

The housing containing the visual feedback system may or may not include a volume controller as previously described.

Figure 11:
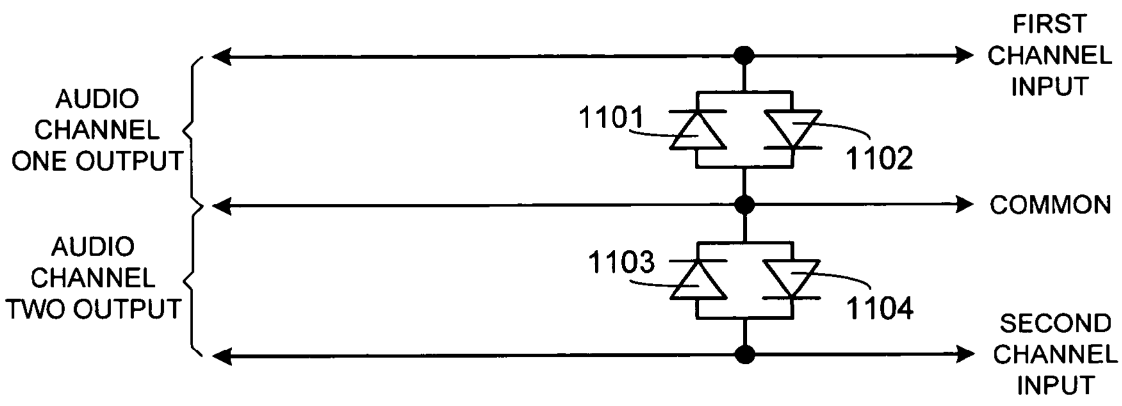
FIG. 11 is an illustration of a simple analog implementation of the invention.

The present invention can utilize either analog or digital circuitry, although it will be appreciated that far greater versatility is provided by the latter. FIG. 11 illustrates an embodiment of a visual feedback system utilizing an analog circuit. As shown, a pair of LEDs 1101/1102 is connected between the signal common line, corresponding to the plug sleeve, and one audio channel, corresponding to the plug tip. A second pair of LEDs 1103/1104 is connected between the signal common line and the second audio channel, corresponding to the plug ring. This arrangement insures that the visual feedback system of the invention will indicate, via the LEDs, when the input signal exceeds the preset level regardless of which channel (i.e., left channel, right channel) receives the excessive signal.

Figure 12:
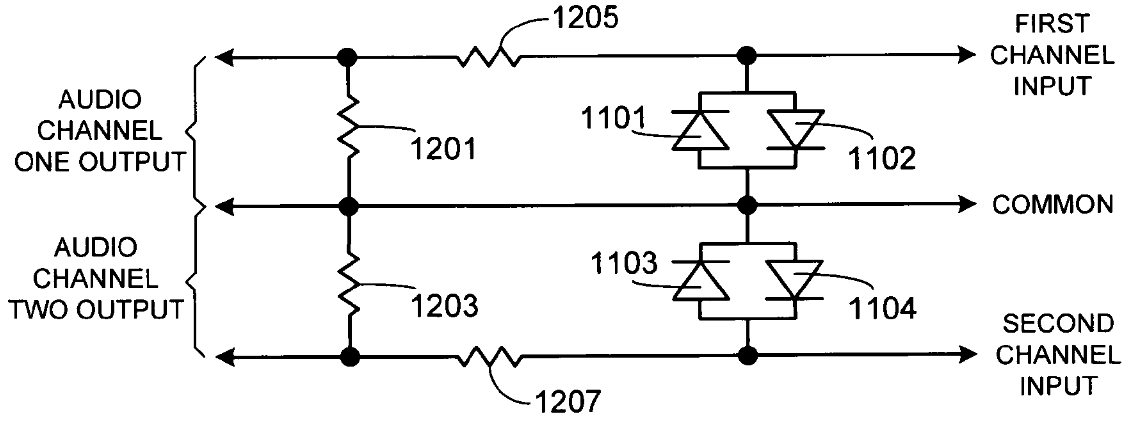
FIG. 12 is an illustration of an analog circuit similar to that shown in FIG. 11, with the addition of signal limiting and headset impedance matching resistors.

FIG. 12 illustrates an alternate embodiment of an analog visual feedback circuit. In addition to the requisite LEDs, this circuit includes resistors 1201 and 1203 that are used to match the visual feedback system to a specific headset impedance. As previously noted, the system can be designed to work with various headsets by including multiple impedance matching resistors and a resistor selection switch (not shown). In this embodiment, additional resistors 1205/1207 are shown, resistors 1205 and 1207 providing a simple means of controlling the preset sound pressure level at which LEDs 1101/1102 and 1103/1104, respectively, turn on.

Although analog circuits such as those shown in FIGS. 11 and 12 can be used to implement the invention, such circuitry has several drawbacks. First, complex systems (e.g., systems capable of calibration using an external microphone, feedback systems with multiple preset levels, etc.) are difficult to implement using analog circuitry. Second, in a typical analog circuit such as those shown in FIGS. 11 and 12, when the LEDs turn on they clip the signal to the speakers. Clipping distorts the incoming signal but does not necessarily reduce it to a level that falls below the preset level. Therefore analog circuits are generally not appropriate if it is desirable to attenuate the incoming signal, in addition to providing a visual indication, after the preset level is reached.

Accordingly in preferred embodiments of the invention, the visual feedback system utilizes digital circuitry, including a digital signal processor (DSP). For example, in the embodiment illustrated in FIG. 13, the incoming signal is input into DSP 1301. DSP 1301 determines if the signal to either channel, assuming a stereo headset with left and right channels 1303/1305 as shown, exceeds the preset level. If the incoming signal(s) exceeds the preset level, DSP 1301 activates visual display 1307.

Figure 14:
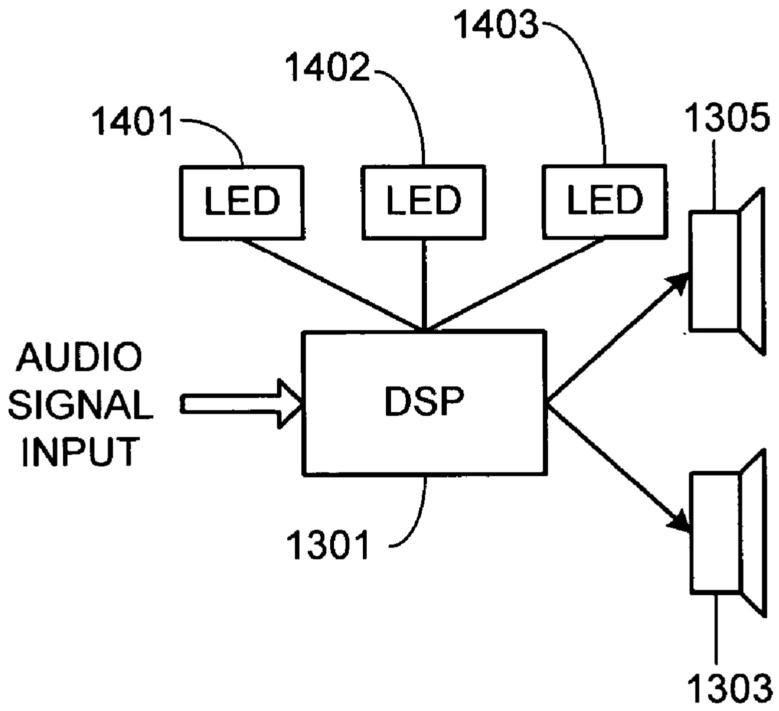
FIG. 14 is an illustration of a digital embodiment utilizing multiple visual indicators, each associated with a different SPL.

An advantage of digital circuitry is that complex systems can be easily implemented. For example, in the embodiment illustrated in FIG. 14, DSP 1301 is connected to three visual displays 1401-1403. In this embodiment, DSP 1301 includes multiple preset volume levels (e.g., 90 dB, 100 dB, 110 dB), each of which activates a different visual display when exceeded. Depending upon the system configuration, visual displays 1401-1403 can be illuminated individually or collectively. If individually illuminated based on the preset level being exceeded, preferably the indicators are of different color (e.g., yellow, orange, red). If illuminated collectively, the number of indicators illuminated can be used to indicate the sound pressure level being exceeded (e.g., one illuminated indicator refers to the lowest level, two illuminated indicators refers to the next level, etc.). Thus a multi-indicator embodiment allows the user to determine the approximate sound level once the lowest preset level is exceeded. For example, if the system includes four preset levels (e.g., 90 dB, 95 dB, 100 dB and 105 dB), once the lowest level is exceeded and until all levels are exceeded, the user knows within 5 dB's the SPL. This is in contrast to an embodiment with a single preset level since in such a system the user has no way of knowing whether they have exceeded the preset level by 1 dB or 30 dB's. As NIHL is the result of both the sound pressure level and the exposure time, multiple preset levels provides a more accurate method for the user to monitor headset use, and thus avoid hearing loss.

In addition to providing a visual indicator when a preset sound pressure level is exceeded, at least one preferred embodiment of the invention attenuates the signal, thereby further protecting the user from NIHL. This is a particularly useful feature for a child's headset. Signal attenuation is simple to implement with a DSP, for example in the embodiments shown in FIGS. 13 and 14, as it simply requires the DSP to attenuate any signal that exceeds a predetermined sound pressure level. This sound level can be the same as the preset level that activates the visual indicator (e.g., display 1307), or set at a different level (e.g., 5 dB above the preset level).

Figure 13:
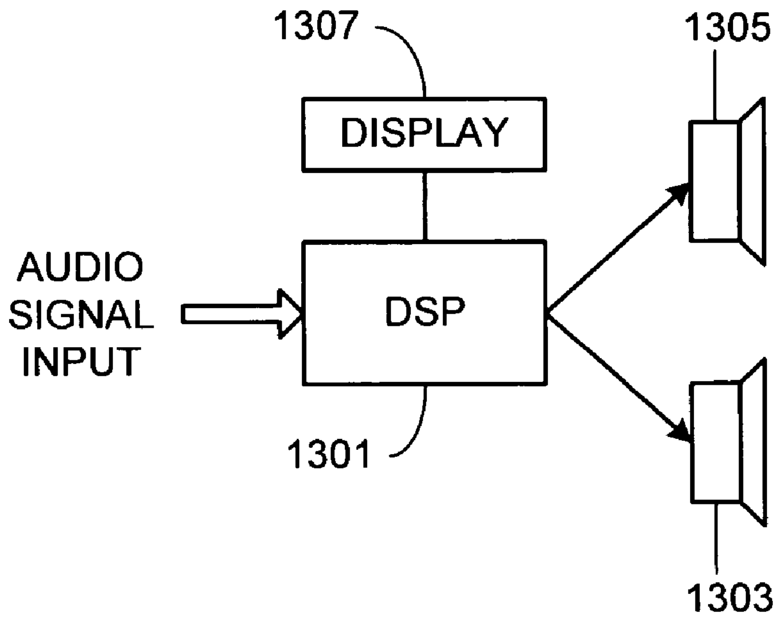
FIG. 13 is an illustration of a simple digital implementation of the invention.
Figure 15:
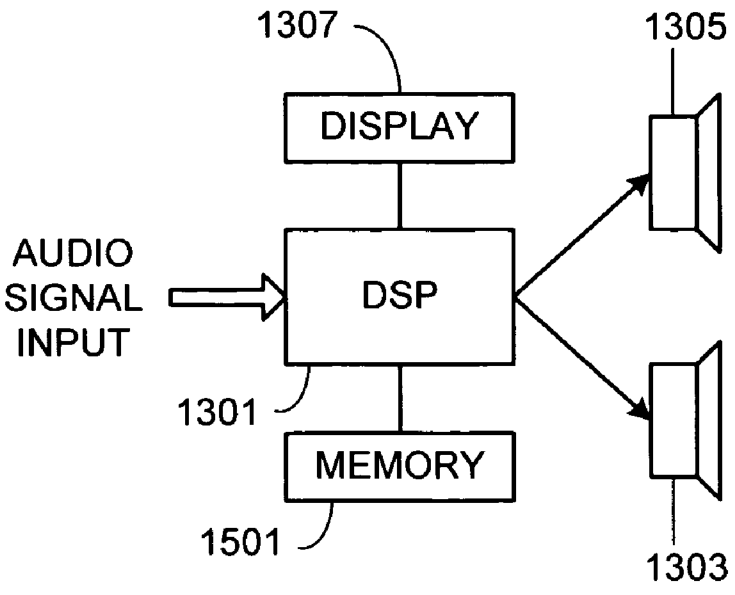
FIG. 15 is an illustration of an embodiment similar to that shown in FIG. 13, except for the inclusion of an extended memory.

FIG. 15 is an illustration of an embodiment similar to that shown in FIG. 13, except for the inclusion of extended memory 1501. Although DSP 1301 includes sufficient memory to record preset levels, etc., in this embodiment extended memory is required to provide sufficient memory for DSP 1301 to maintain a history of each time the SPL exceeded the preset level(s). As NIHL is dependent upon both the sound pressure and the exposure time, preferably for each SPL excursion above the preset level, DSP 1301 logs the length of time the SPL exceeded the preset level and by how much the level was exceeded. This information is particularly useful for individuals who may need to routinely exceed the preset level, for example sound engineers.

Figure 16:
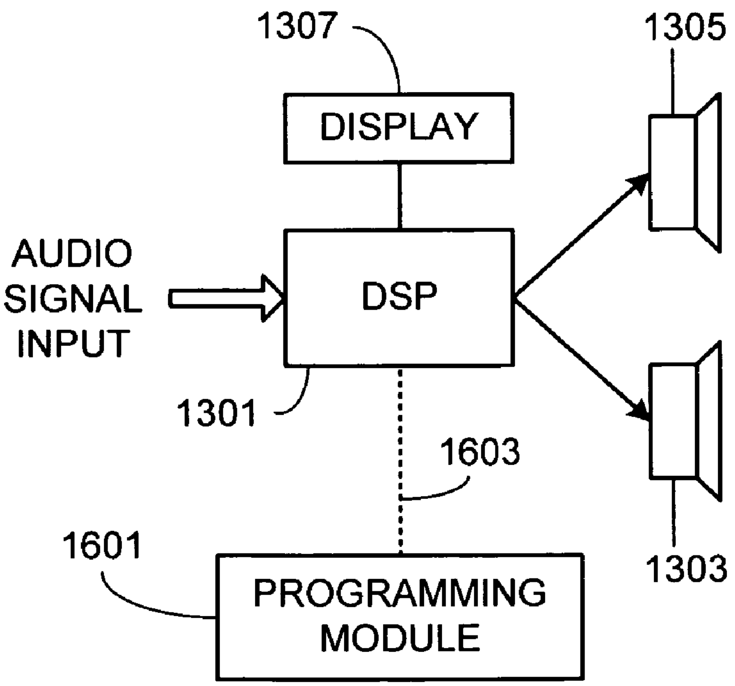
FIG. 16 is an illustration of an alternate embodiment similar to that shown in FIG. 13, except for the inclusion of a programming module.
Figure 17:
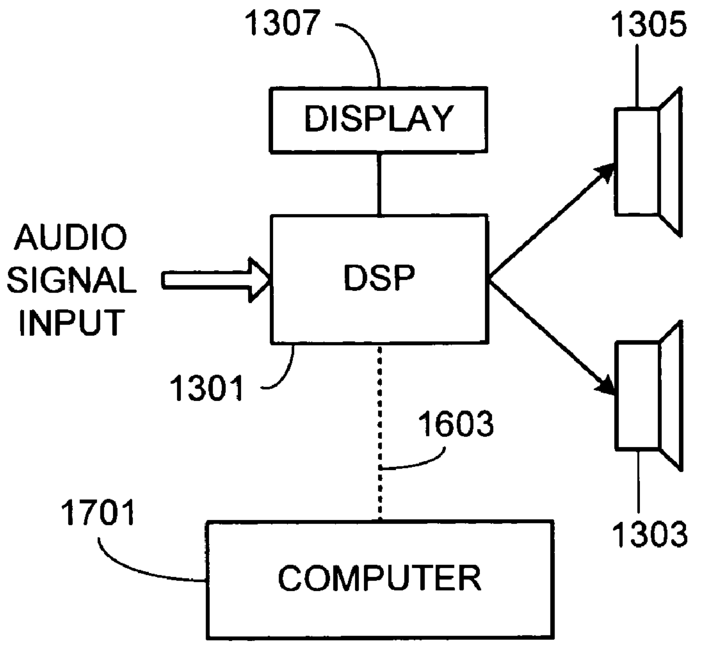
FIG. 17 is an illustration of an alternate embodiment similar to that shown in FIG. 16 wherein the functions of the programming module are performed via a computer.

FIG. 16 is an illustration of an alternate embodiment similar to that shown in FIG. 13, except for the inclusion of a programming module 1601. Preferably programming module 1601 is coupled to the visual feedback system and DSP 1301 via a removable cable 1603, thereby allowing the visual feedback system to be contained within an extremely small housing while still providing the user with the ability to set many of the operating parameters of the DSP. Although in the preferred embodiment all DSP programming is performed using programming module 1601, it will be appreciated that this same function can be performed using a computer 1701 coupled to the visual feedback system using cable 1603 as shown in FIG. 17. Programming module 1601, or alternately computer 1701, is used to program any of the functions of the DSP such as SPL preset level (or levels if multiple LEDs representing multiple levels are coupled to the DSP), attenuation (e.g., on/off, turn-on SPL if different than the preset level), log capabilities, and log read-out. If the visual feedback system is not hard-wired to a specific set of headsets, for example as discussed relative to FIGS. 5 and 6, the programming module 1601, or computer 1701, is also used to match the performance of DSP 1301 to a particular headset. In one approach headset matching is performed using a look-up table. The look-up table includes both headset performance specifications (e.g., headset impedance) as well as specific headset descriptors (e.g., manufacturer and model number). Preferably the look-up table is updateable, for example by downloading via either an Internet connection or other means. In a second approach, headset matching is performed using a calibration microphone, for example as described relative to FIGS. 8-10.

Figure 18:
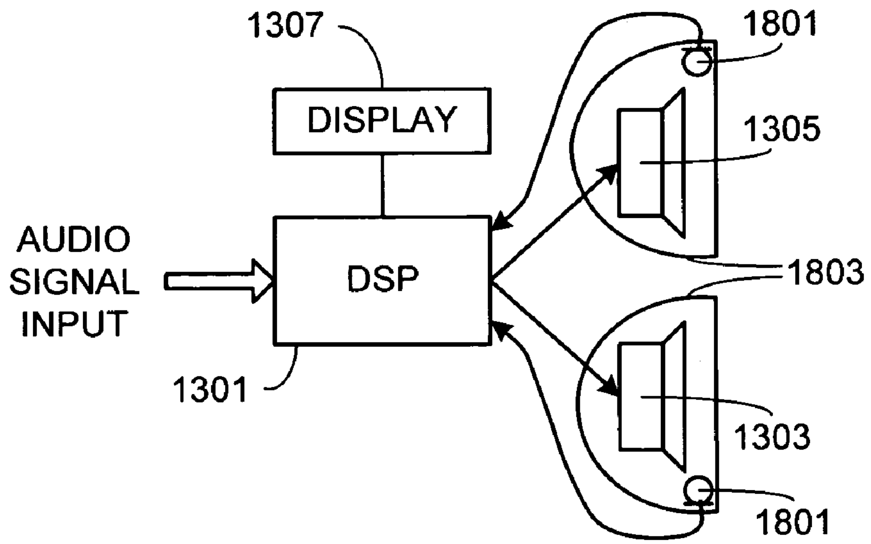
FIG. 18 is an illustration of an alternate embodiment similar to that shown in FIG. 13, except for the inclusion of a microphone embedded within each headset earpiece.

As previously noted, the use of digital circuitry in general, and DSP 1301 in particular, allows the implementation of relatively complex systems. For example in the embodiment illustrated in FIG. 18, as opposed to comparing the incoming signal level to the preset level in order to determine when the SPL is excessive, actual sound pressure levels are used to determine when the preset level has been exceeded. As shown, a monitoring microphone 1801 is embedded into one, or preferably both, headset earpieces 1803. Whenever the sound pressure level received by microphone 1801 exceeds the preset level, visual display 1307 is activated.

As will be understood by those familiar with the art, the present invention may be embodied in other specific forms without departing from the spirit or essential characteristics thereof. Accordingly, the disclosures and descriptions herein are intended to be illustrative, but not limiting, of the scope of the invention which is set forth in the following claims.

What is claimed is:

1. A visual feedback system comprising:

a headset coupleable to an audio source, wherein said headset receives an electrical signal from said audio source, wherein said electrical signal represents a sound to be generated by said headset, wherein said audio source is external and independent from said headset, and wherein said audio source is a music player;

a signal processor for comparing said electrical signal to a plurality of preset signal levels, wherein each of said preset signal levels corresponds to a different sound pressure level, and wherein said signal processor monitors a duration said electrical signal exceeds each of said plurality of preset signal levels;

a memory coupled to said signal processor, wherein said signal processor stores within said memory a log corresponding to said duration that said electrical signal exceeds each of said plurality of preset signal levels;

a display coupled to said signal processor, wherein said display includes a plurality of distinguishable display features which may be selectively activated by said signal processor, wherein each of said plurality of distinguishable display features correspond to each of said plurality of preset signal levels, wherein said signal processor activates a corresponding one of said plurality of distinguishable display features when said electrical signal exceeds a corresponding one of said plurality of preset signal levels; and a calibration microphone, wherein said calibration microphone is adapted to be coupleable to said headset, wherein during a calibration process said calibration microphone simulates a headset user and monitors said sound generated by said headset in order to calibrate said visual feedback system.

2. The visual feedback system of claim 1, wherein said headset is coupleable to said audio source via a headphone plug.

3. The visual feedback system of claim 1, further comprising a headset housing, said headset housing containing said signal processor, said memory, said display, and a volume controller, wherein said volume controller controls a signal level corresponding to said electrical signal.

4. The visual feedback system of claim 1, wherein said display further comprises a plurality of light emitting diodes, wherein said plurality of light emitting diodes correspond to said plurality of distinguishable display features.

5. The visual feedback system of claim 1, further comprising means for attenuating said electrical signal each time said electrical signal exceeds one of said plurality of preset signal levels.

6. The visual feedback system of claim 1, further comprising an impedance selector switch for matching said visual feedback system to a headset impedance.

7. The visual feedback system of claim 1, wherein said calibration microphone is comprised of a first channel calibration microphone and a second channel calibration microphone.

8. The visual feedback system of claim 7, further comprising an ear simulator, wherein said first channel calibration microphone and said second calibration microphone are housed within said ear simulator.

9. A visual feedback system comprising:

a headset coupleable to an audio source, wherein said headset receives an electrical signal from said audio source, wherein said electrical signal represents a sound to be generated by said headset, wherein said audio source is external and independent from said headset, and wherein said audio source is a music player a signal processor for comparing said electrical signal to a plurality of preset signal levels, wherein each of said preset signal levels corresponds to a different sound pressure level;

a display coupled to said signal processor, wherein said display includes a plurality of distinguishable display features which may be selectively activated by said signal processor, wherein said plurality of distinguishable display features correspond to said plurality of preset signal levels, wherein said signal processor activates a corresponding one of said plurality of distinguishable display features when said electrical signal exceeds a corresponding one of said plurality of preset signal levels;

a calibration microphone, wherein said calibration microphone is adapted to be coupleable to said headset, wherein during a calibration process said calibration microphone simulates a headset user and monitors said sound generated by said headset in order to calibrate said visual feedback system.

10. The visual feedback system of claim 9, wherein said calibration microphone is comprised of a first channel calibration microphone and a second channel calibration microphone.

11. The visual feedback system of claim 10, further comprising an ear simulator, wherein said first channel calibration microphone and said second calibration microphone are housed within said ear simulator.

12. The visual feedback system of claim 9, wherein said signal processor monitors a duration said electrical signa exceeds each of said plurality of preset signal levels, said visual feedback system further comprising a memory coupled to said signal processor, wherein said signal processor stores within said memory a log corresponding to said duration that said electrical signal exceeds each of said plurality of preset signal levels.

13. The visual feedback system of claim 9, further comprising means for attenuating said electrical signal from said audio source each time said electrical signal exceeds one of said plurality of preset signal levels.

14. The visual feedback system of claim 9, wherein said headset is coupleable to said audio source via a headphone plug.

15. The visual feedback system of claim 9, further comprising a headset housing, said headset housing containing said signal processor, said display, and a volume controller, wherein said volume controller controls a signal level corresponding to said electrical signal.

16. The visual feedback system of claim 9, wherein said display further comprises a plurality of light emitting diodes, wherein said plurality of light emitting diodes correspond to said plurality of distinguishable display features.

17. The visual feedback system of claim 9, further comprising an impedance selector switch for matching said visual feedback system to a headset impedance.

* * * * *